United States Patent [19]

Schneider et al.

[11] Patent Number: 5,238,557
[45] Date of Patent: Aug. 24, 1993

[54] APPARATUS FOR CONTROLLING THE TEMPERATURE OF THE MOBILE PHASE IN A FLUID CHROMATOGRAPH

[75] Inventors: Werner Schneider, Ettlingen; Klaus Witt, Keltern, both of

[73] Assignee: Hewlett Packard Company, Palo Alto, Calif.

[21] Appl. No.: 966,596

[22] Filed: Oct. 26, 1992

Related U.S. Application Data

[63] Continuation of Ser. No. 643,794, Jan. 22, 1991, abandoned.

[30] Foreign Application Priority Data

Jan. 24, 1990 [EP] European Pat. Off. ........ 90101385.4

[51] Int. Cl.⁵ .................................................. B01D 15/08
[52] U.S. Cl. ............................. 210/198.2; 210/143; 210/181; 210/656; 165/164
[58] Field of Search ............... 210/656, 657, 658, 659, 210/143, 181, 198.2; 165/164

[56] References Cited

U.S. PATENT DOCUMENTS

| | | | |
|---|---|---|---|
| 3,449,938 | 6/1969 | Giddings | 210/198.2 |
| 3,522,725 | 8/1970 | Waters | 210/656 |
| 3,760,481 | 9/1973 | Greever | 29/890.043 |
| 4,019,372 | 4/1977 | Parkell | 210/198.2 |
| 4,098,592 | 7/1978 | Prescott | 210/198.2 |
| 4,147,037 | 4/1979 | Gelbard | 165/171 |
| 4,181,613 | 1/1980 | Welsh | 210/198.2 |
| 4,404,845 | 9/1983 | Schrenker | 210/198.2 |
| 4,484,061 | 11/1984 | Zelinka | 210/198.2 |
| 4,554,436 | 11/1985 | Chlosta | 210/657 |
| 4,599,169 | 7/1986 | Ray | 210/198.2 |
| 4,726,822 | 2/1988 | Cates | 210/198.2 |
| 4,917,575 | 4/1990 | Miller | 210/198.2 |
| 4,918,942 | 4/1990 | Jaster | 62/510 |
| 4,966,695 | 10/1990 | Joshua | 210/198.2 |
| 5,024,758 | 6/1991 | Ito | 210/198.2 |
| 5,038,852 | 8/1991 | Johnson | 162/12 |

FOREIGN PATENT DOCUMENTS

| | | | |
|---|---|---|---|
| 10043946 | 6/1981 | European Pat. Off. | 210/198.2 |
| 2306093 | 9/1974 | Fed. Rep. of Germany | 210/198.2 |
| 8536810 | 12/1986 | Fed. Rep. of Germany | 210/198.2 |
| 2068539 | 8/1981 | United Kingdom | 210/198.2 |

*Primary Examiner*—Ernest G. Therkorn

[57] ABSTRACT

Apparatus for controlling the temperature of a mobile phase in a fluid chromatographic system are provided which comprise both an ingoing capillary connected to an inlet of a column and an outgoing capillary connected an outlet of the column. A portion of the ingoing capillary and a portion of the outgoing capillary are arranged in thermal contact with each other to form a contact region wherein heat exchange can occur. In preferred embodiments, liquid leaving the column at an elevated temperature loses a portion of its heat, thus avoiding or at least substantially reducing the transfer of heat to the detector. At the same time, liquid flowing to the column is pre-heated by the liquid leaving the column so that the heating power required for bringing the mobile phase to the desired temperature is reduced as compared with prior art devices.

20 Claims, 3 Drawing Sheets

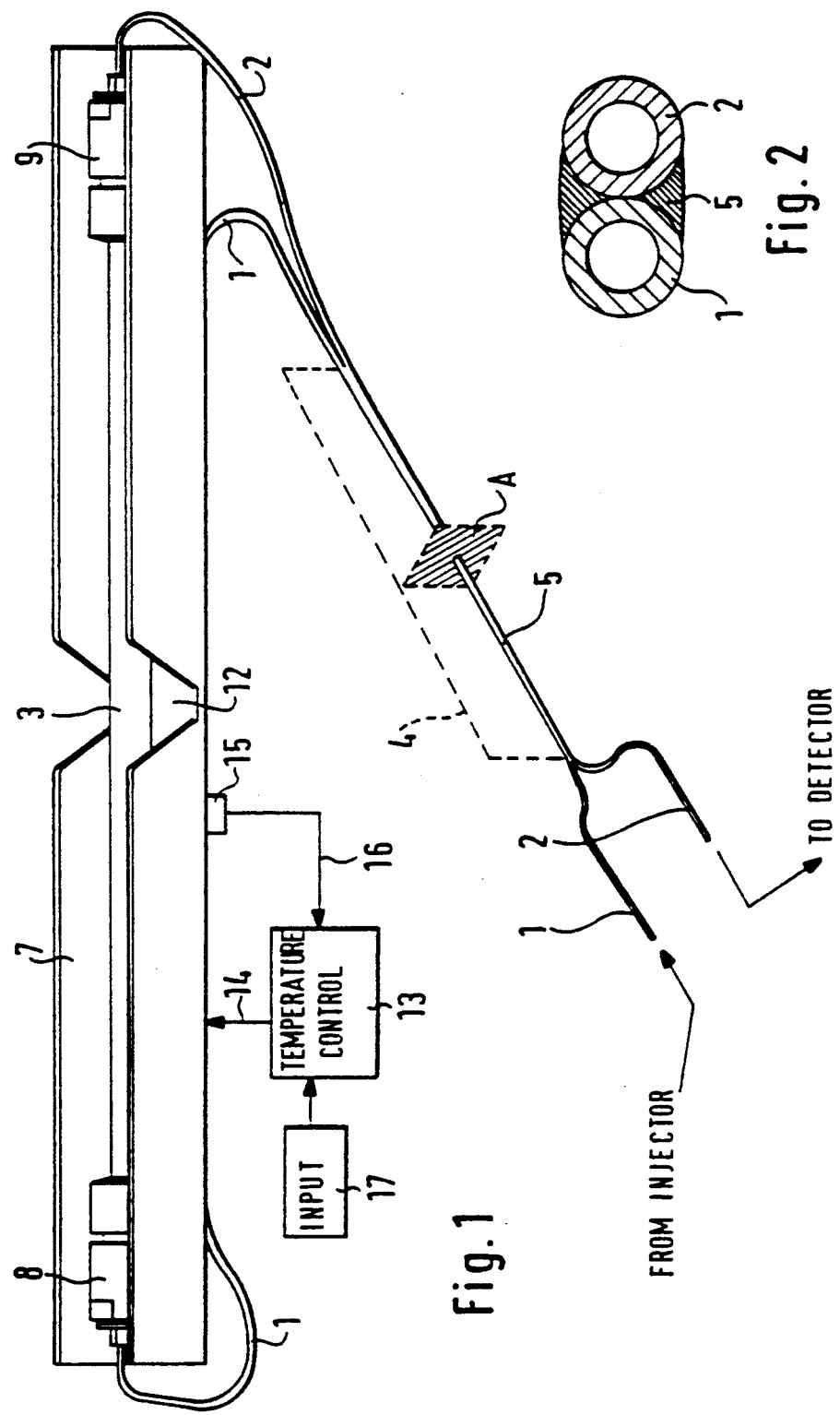

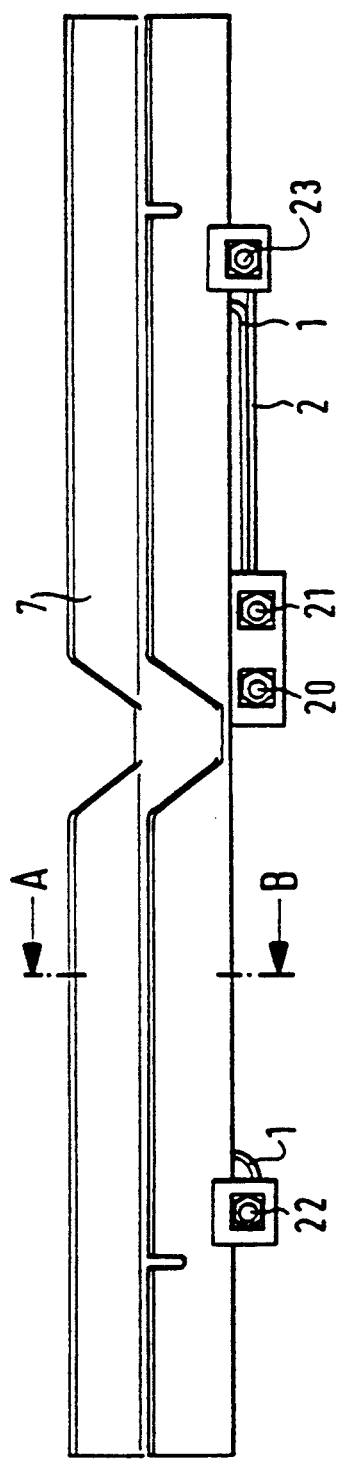
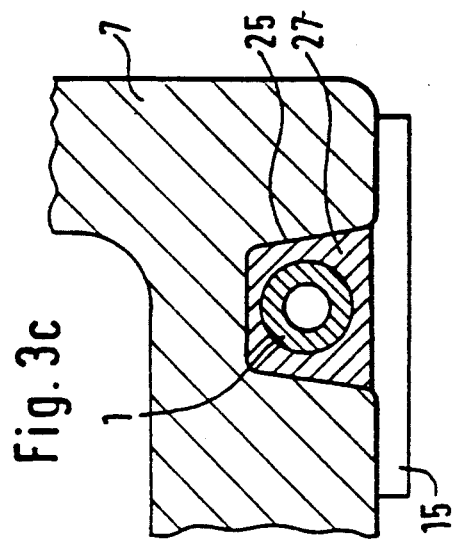
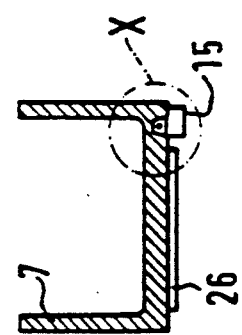

APPARATUS FOR CONTROLLING THE TEMPERATURE OF THE MOBILE PHASE IN A FLUID CHROMATOGRAPH

This is a continuation of application Ser. No. 643,794 filed Jan. 22, 1991, now abandoned.

BACKGROUND OF THE INVENTION

This invention relates to an apparatus for controlling the temperature of the mobile phase in a fluid chromatographic system and, more particularly, to an apparatus wherein such temperature control is effected as the mobile phase enters and exits a liquid chromatographic column.

It is known that the separation process in the column of a liquid chromatograph is temperature dependent. That is, the chromatographic retention times of sample substances to be analyzed are a function of temperature. It is also known that the separation of the various substances in a chromatographic sample, known as the chromatographic resolution power, is also a function of temperature. Thus, temperature selection can be used in a systematic manner to adjust and optimize conditions for a specific separation problem. For example, there are known chromatographs which comprise means to adapt the temperature of an incoming solvent stream to that of the column to minimize chromatographically disturbing temperature gradients in the column bed. In many chromatographic applications, a temperature in the range between 25° C. and 100° C. is used. One device for controlling the temperature of the chromatographic mobile phase is disclosed by European Application EP-A1 0 043 946. In this apparatus, the separation column is arranged in a housing of heat insulating material in which air is circulated with a fan. The air circulating in the housing is heated as it flows past an electrical heating element; thereafter, the air flows past the column and brings it to an elevated temperature. In order to achieve pre-heating of the liquid flowing into the column, a portion of an ingoing capillary connected to the column entrance is arranged inside the heating element. The solvent stream leaving the column with the separated sample substances is then conducted to a suitable detector, for example to a photometric absorbance detector.

Many detectors used in liquid chromatography are temperature sensitive. The accuracy of these detectors can be significantly impaired by temperature effects. One common problem involves refractive index variations caused by differences between the temperatures of the solvent and the temperature of the detector. These variations lead to noise in the measured absorbance signal. Unfortunately, the level of this noise gets higher as the temperature difference between the solvent and the detector increases.

A further concern in liquid chromatography is external band spreading, which impairs chromatographic selectivity and resolution. External band spreading can be minimized by making the connection between the column outlet and the detector as short as possible. By maintaining a relatively short path between the column outlet and the detector, however, the solvent exiting a column operated at elevated temperature typically is hot enough upon reaching the detector to produce the above mentioned noise. On common way to cope with this problem is to provide the detector with extra heat exchangers which reduce the temperature difference by dissipating at least a portion of the heat into the air surrounding the detector. This approach, however, requires extra capillary tubes, which results in higher external bandspreading and makes the instrument more complex and costly.

Accordingly, there exists need for an apparatus for controlling the temperature of a liquid chromatographic mobile phase which has a less complex design and which at least reduces the problems associated with heat transfer.

SUMMARY OF THE INVENTION

The present invention provides an improved apparatus for thermostating the mobile phase in a fluid chromatographic system which comprise both an ingoing capillary connected to an inlet of a column and an outgoing capillary connected an outlet of the column. In the apparatus of the present invention, a portion of the ingoing capillary and a portion of the outgoing capillary are arranged in thermal contact with each other to form a contact region wherein heat exchange can occur. In this arrangement, a fluid—preferably a liquid—leaving the column at an elevated temperature loses a portion of its heat, thus avoiding or at least substantially reducing the transfer of heat to the detector. At the same time, the liquid flowing to the column is pre-heated by the liquid leaving the column so that the heating power required for bringing the mobile phase to a desired temperature is reduced as compared with prior art devices.

According to preferred embodiments, the column is held in thermal contact with a receiving piece which can be heated to a desired temperature by a temperature influencing means. Since the ingoing and outgoing capillaries are thermally coupled, heating the column also pre-heats the liquid entering the column.

In other preferred embodiments, thermal contact is effected by soldering two circular capillaries together at their walls. This arrangement has the advantage that it is very simple to manufacture and does not require extra parts. According to another embodiment, the capillaries have an elongated cross sectional shape so that the contact area in the heat exchanging region is increased.

The invention is also of particular advantage when the column is cooled to extend its working temperature range. Typical cooling elements, for example Peltier elements, have a comparatively small efficiency, so that a recovery of cooling power is particularly important in order to keep the power consumption and the requirements regarding power electronics small.

In embodiments wherein the mobile phase is to be heated, the temperature influencing means can be a flat-foil heating element attached to the receiving piece. The temperature influencing means may comprise a control loop having a temperature sensor in contact with the receiving piece and a controllable current source providing a current output to a resistance heating means in response to the difference between the measured temperature and a desired temperature. Preferably, control of the current supplied to the resistance heating is achieved using pulse width modulation, which has the advantage that it leads to a decreased power consumption.

To achieve a even more efficient transfer of thermal energy to the incoming mobile phase, the incoming capillary is arranged in a recess of the receiving piece and the recess is filled with solder. In order to rapid adjustment and control of the mobile phase temperature, a temperature sensor is positioned in close proximity to the incoming capillary.

BRIEF DESCRIPTION OF THE DRAWINGS

The numerous objects and advantages of the present invention may be better understood by those skilled in the art by reference to the accompanying figures, in which:

FIG. 1 schematically shows a preferred apparatus of the present invention, partially in a perspective view.

FIG. 2 shows a cross-section along the plane A shown in FIG. 1.

FIG. 3a shows a portion of the apparatus of FIG. 1 in greater detail.

FIG. 3b shows a cross-section along the line A—B in FIG. 3a.

FIG. 3c is a magnified view of the detail X in FIG. 3b.

DETAILED DESCRIPTION OF THE INVENTION

Figure 4A:
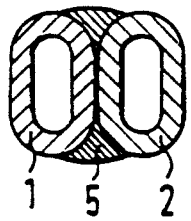
FIGS. 4a-4c show three alternative embodiments for the connection of the two capillary tubes in the plane A indicated in FIG. 1.

FIG. 1 shows a preferred apparatus for controlling the temperature of the mobile phase in a liquid chromatograph. Separation column 3, which has the shape of a cylinder, is positioned in elongated receiving piece 7, which has a U-shaped cross-section, or some other suitable receiving means. Receiving piece 7 is made of a material such as aluminum which has good thermal conductivity. Column 3, which typically comprises an tube fabricated from stainless steel or some other metal, is arranged in good thermal contact with receiving piece 7. As shown in FIG. 1, receiving piece 7 comprises a recess 12 to permit easy removal of the column by an operator.

In preferred embodiments, receiving piece 7 is connected to a temperature influencing means by which the receiving piece and, hence, column 3 can be brought to a desired temperature above or below ambient temperature. In one embodiment of the invention, the temperature influencing means comprises an electrically resistive heating element positioned at the mean portion of piece 7 on the side opposite the U-shaped opening. Preferably, the heating means comprises a flat-foil heating element with conductive paths embedded in a thin foil.

The heat generated in receiving piece 7 by the heating means can be controlled by current supplied from temperature control unit 13 via line 14. The supply of current from unit 13 occurs in response to the actual temperature of piece 7 measured by a temperature sensor 15 which is in thermal contact with piece 7. A desired temperature value can be adjusted by the user via input means 17. A signal corresponding to this desired value is compared by temperature control unit 13 with the signal supplied via line 16, which corresponds to the actual, measured temperature. The current supplied to the heating means is then controlled in response to the difference between the desired and actual values. According to a preferred embodiment of the invention, temperature control unit 13 operates in a pulse width control mode wherein current is supplied to the heating means as pulses having fixed frequency but variable pulse width. The pulse width is adjusted by control unit 13 such that the temperature of piece 7 is maintained at the desired value. For example, the pulses can occur at a fixed rate of 30 kHz with a pulse width of up to 32 microseconds. The pulse width control mode has the advantage that it has a reduced power consumption as compared to other control modes.

According to another embodiment of the invention, a combined heating and cooling system in thermal contact with the metal piece 7 is provided which permits the adjustment of temperatures above as well as below ambient temperature. In this embodiment, the cooling elements could, for example, be Peltier elements.

As shown in FIG. 1, column 3 preferably comprises end fittings 8 and 9 for connecting capillary tubes 1 and 2, respectively, to the column. Capillary 1 is the ingoing capillary through which solvent and a sample to be chromatographically analyzed are introduced into the column, while capillary 2 is the outgoing capillary through which the solvent and the chromatographically separated sample leaves the column and is fed to a detector such as a photometric detector, a fluorescence detector, an electrochemical detector, or a refractive index detector. As in FIG. 1, ingoing capillary 1 is arranged in good thermal contact with the bottom side of the piece 7, as will be explained in greater detail with reference to FIGS. 3b and 3c.

According to a preferred embodiment, capillaries 1 and 2 are in contact with each other in region 4 such that good heat transfer between the two capillaries is possible. In the embodiment shown in FIG. 1, the two capillaries are brought into thermal contact with each other and are connected by means of solder 5. It will be recognized that thermal contact may or may not include physical contact but does require thermal communication. Region 4, in which the capillaries are connected with each other, typically has a length of approximately 13 cm. Thus, in chromatographic applications wherein the mobile phase is to be heated, liquid leaving column 3 through outgoing capillary 2 transfers a portion of its heat to the liquid flowing to the column in ingoing capillary 1. In this way, the liquid to the column is pre-heated so that less heating power is required by the heating means of piece 7. Furthermore, the temperature of the liquid leaving the column is reduced so that the amount of heat transported to the detector is reduced.

FIG. 2 shows a cross-section along the plane A perpendicular to the longitudinal axis of the capillaries. This illustrates the manner in which the capillaries are connected in region 4. As shown in FIG. 2, capillaries 1 and 2 have a circular cross-section and are in contact at their periphery. In certain preferred embodiments, the capillaries each have an internal diameter of about 0.17 mm and an outer diameter of about 0.6 mm. The gap between the capillaries is filled with solder 5, which establishes a fixed point of connection between the capillaries and at the same time increases the thermal coupling therebetween. The capillaries can be arranged parallel to each other in region 4 or, alternatively, may be twisted with a few turns over the length of this region. Capillaries 1 and 2 preferably are fabricated from a metal such as titanium or tantalum, more preferably, from stainless steel.

In preferred embodiments, apparatus according to the present invention are positioned in the housing of a liquid chromatography module. In these embodiments, the free ends of capillaries 1 and 2 are equipped with tube fittings so that the injector of the liquid chromatograph can be connected to capillary 1, and capillary 2 can be connected to a suitable detector. For example, FIG. 3a shows a receiving piece 7 which bears an input fitting 20 for connection to an injector and an output fitting 21 for connection to a detector. Fittings 22 and 23 are positioned at the left and right lower side of piece 7, respectively, to receive the capillaries (not shown) connected to the entrance and exit of the chromatographic column, respectively. Connected to the rear side of fitting 23 is capillary 2, which is connected with its other end to the rear side of output fitting 21. Capillary 1 is connected to the rear side of input fitting 20 and is arranged in thermal contact with capillary 2 along the indicated distance between fittings 21 and 23. This area of thermal contact between the two capillaries corresponds to the region 4 shown in FIG. 1. Capillary 1 extends along the bottom of piece 7 up to the rear side of fitting 22, to which it preferably is fixed.

FIG. 3b shows a cross-sectional view along line A-B in FIG. 3a. FIG. 3c shows an enlarged view of region X in FIG. 3b and illustrates how capillary 1 is arranged in the bottom of receiving piece 7. As can be seen from FIG. 3c, capillary 1 extends in a recess 25 of the piece 7. Recess 25 is filled with solder 27 to provide good mechanical connection and thermal contact with piece 7. Flat-foil heating element 26 is attached to the bottom of piece 7 in thermal contact therewith, as shown in FIG. 3b. The foil extends over substantially the entire length of piece 7. Temperature sensor 15 is positioned beside heater foil 26 below recess 25, as shown in FIG. 3c. Thus, temperature sensor 15 is proximate the mobile phase flow, so that rapidly responsive control of the mobile phase temperature is ensured.

Figure 4B:
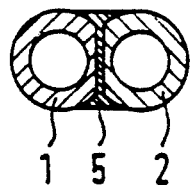
Figure 4C:
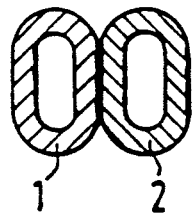

FIGS. 4a–4c show three alternative embodiments for the connection of capillaries in region 4. Each of these figures corresponds to a cross-section in the plane A illustrated in FIG. 1. According to FIG. 4a, the capillaries have an elongated or oval cross-sectional profile with substantially flat walls so that the contact area therebetween is greater than in case of capillaries having a circular cross-section, thus contributing to more efficient heat exchange (i.e., thermal communication) between the capillaries. Another way to improve the thermal contact between two circular capillaries is shown in FIG. 4b, wherein a portion of each capillary circular wall has been removed to form a substantially flat wall. By joining the capillaries where the material has been removed, the contact area between the two capillaries is increased and the wall thickness is reduced; both measures contribute to improved heat transfer. In the embodiments shown in FIGS. 4a and 4b, the gaps between the capillaries are filled with solder 5 to establish a fixed connection between the capillaries and to improve their thermal coupling. In the embodiment of FIG. 4c, no additional material such as solder 5 is required, but capillaries 1 and 2 are directly connected via their walls by means of, for example, laser or electron beam welding.

In order to obtain good heat exchange between ingoing and outgoing capillaries in their contact region, it is important to keep the thermal resistance between the ingoing and outgoing liquid paths as small as possible. This may be accomplished by employing materials which have high thermal conductivity in fabricating apparatus components such as the capillaries. Heat exchange, however, is also influenced by the general environment of the capillaries due to secondary thermal paths. For example, heat conduction can occur through the surrounding air or by heat radiation. To reduce these influences, capillaries 1 and 2 in region 4 preferably are thermally insulated from the environment. For example, the capillaries can be embedded in heat insulating material or they can be positioned in an evacuated housing to preventing heat conduction through the air.

Figure 5:
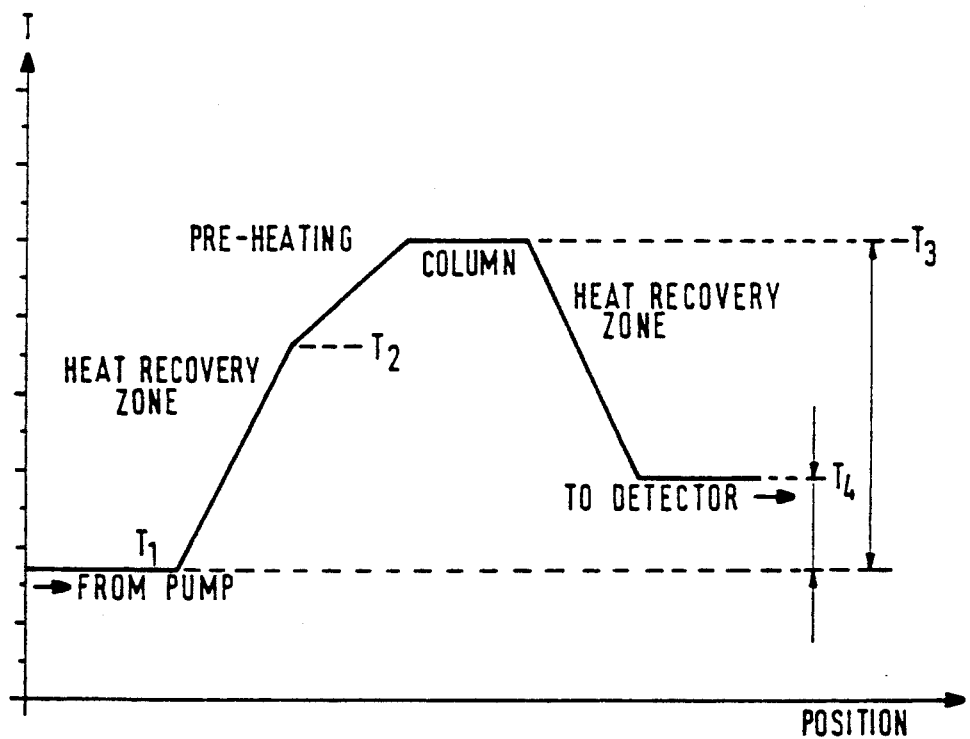
FIG. 5 shows a typical temperature curve for the mobile phase at various locations in the apparatus of FIG. 1.

FIG. 5 shows a typical temperature curve for a mobile phase flowing through an apparatus according to the present invention wherein the mobile phase is heated above ambient temperature. The horizontal axis shows the position of the mobile phase in the apparatus, while the vertical axis shows the corresponding temperature of the mobile phase at that position. As can be seen, the mobile phase enters the apparatus at, for example, fitting 20 from, for example, an injection port with a temperature $T_1$. In region 4 wherein the ingoing and the outgoing capillary are in contact with each other, the temperature rises continuously from $T_1$ to $T_2$, represented in FIG. 5 by the portion labelled "Heat Recovery Zone". The portion of the curve labelled "Pre-heating" corresponds to the section of the capillary system arranged in the recess of piece 7, wherein the temperature of the mobile phase is brought to its highest value, $T_3$, at the entrance of the chromatographic column. During its passage through the column, the temperature remains substantially constant at the value $T_3$. Then, in the region 4 wherein outgoing capillary 2 is in contact with ingoing capillary 1, the mobile phase leaving the column gives off heat so that the temperature drops from $T_3$ to $T_4$, which is the temperature with which the mobile phase flows to the detector.

Thus, by maintaining the ingoing and outgoing capillaries in contact with each other along a certain portion of their length, an efficient heat exchange can be achieved. The apparatus of the present invention has a very simple design which employs components found in many, if not most, liquid chromatographs, namely the ingoing and outgoing capillaries. According to preferred embodiments, no additional tubing is required; thus, further external band spreading is minimized. The apparatus of the invention provides very efficient heat exchange because the heat exchange between inflowing and outflowing liquids is much more efficient than the heat exchange between liquid and air, as in many known devices. Also, the use of capillaries with small internal diameter results in substantially enhanced heat transmission from the capillary walls to the mobile phase. Due to the efficient heat exchange achieved by the invention, the power required for the adjustment of a desired temperature is comparatively small.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. An apparatus for controlling the temperature of a mobile phase in a fluid chromatographic system which comprises:
   a chromatographic column;
   temperature influencing means for heating or cooling the column;

an ingoing capillary fabricated from thermally conductive material connected at a first end to an inlet of the column; and an outgoing capillary fabricated from thermally conductive material connected at a first end to an outlet of the column;

a portion of the ingoing capillary and a portion of the outgoing capillary being arranged in thermal contact with each other to form a contact region wherein heat is exchanged between the ingoing capillary and the outgoing capillary with minimized influence from elements other than the capillaries.

2. The apparatus of claim 1 wherein the fluid is a liquid.

3. The apparatus of claim 1 wherein a temperature sensor is positioned adjacent the ingoing capillary.

4. The apparatus of claim 1 further comprising a receiving means in thermal contact with the column.

5. The apparatus of claim 4 wherein the temperature influencing means comprise an electrically resistive element.

6. The apparatus of claim 4 wherein the temperature influencing means comprises a cooling element.

7. The apparatus of claim 6 wherein the cooling element is a Peltier element.

8. The apparatus of claim 4 wherein the temperature influencing means comprises a flat-foil heating element attached to the receiving means.

9. The apparatus of claim 8 further comprising pulse width modulation circuitry for supplying current pulses of predetermined width to the heating element.

10. The apparatus of claim 9 wherein the widths of the current pulses are controlled in response to an actual temperature value measured by a temperature sensor connected to the receiving means, such that the receiving means is maintained at a desired temperature.

11. The apparatus of claim 4 wherein the receiving means includes a recess and a portion of the ingoing capillary is arranged in the recess.

12. The apparatus of claim 4 wherein the receiving means comprises metal.

13. The apparatus of claim 4 wherein the column is positioned in the interior of the receiving means.

14. The apparatus of claim 1 wherein the ingoing capillary and the outgoing capillary each have a substantially circular cross-section within at least a portion of the thermal contact region.

15. The apparatus of claim 1 further comprising solder between the ingoing capillary and the outgoing capillary in the thermal contact region.

16. The apparatus of claim 1 wherein the ingoing capillary and the outgoing capillary have substantially flat walls in thermal contact with one another within at least a portion of the contact region.

17. The apparatus of claim 1 wherein the ingoing capillary is connected at a second end to an injection port.

18. The apparatus of claim 1 wherein the outgoing capillary is connected at a second end to means for receiving said mobile phase from said outgoing capillary, said means for receiving said mobile phase being substantially thermally decoupled from said temperature influencing means.

19. The apparatus of claim 18 wherein said means for receiving said mobile phase is a chromatographic detector.

20. An apparatus for controlling the temperature of a mobile phase in a liquid chromatograph which comprises:

an ingoing capillary fabricated from thermally conductive material connected at a first end to an inlet of a column and at a second end to an injection port;

an outgoing capillary fabricated from thermally conductive material connected at a first end to an outlet of the column and at a second end to a detector;

a receiving means in thermal contact with the column; and temperature influencing means for heating or cooling the receiving means;

a portion of the ingoing capillary and a portion of the outgoing capillary being arranged in thermal contact with each other to form a thermal contact region wherein heat is exchanged between the ingoing capillary and the outgoing capillary with minimized influence from elements other than the capillaries.

* * * * *

UNITED STATES PATENT AND TRADEMARK OFFICE
CERTIFICATE OF CORRECTION

PATENT NO. : 5,238,557
DATED : August 24, 1993
INVENTOR(S) : Werner SCHNEIDER et al.

It is certified that error appears in the above-indentified patent and that said Letters Patent is hereby corrected as shown below:

On the title page, item [75] Inventors: insert;
--Federal Republic of Germany-- after "of".

Signed and Sealed this

Thirtieth Day of July, 1996

Attest:

BRUCE LEHMAN

*Attesting Officer*   *Commissioner of Patents and Trademarks*